(12) United States Patent
Jeong et al.

(10) Patent No.: US 8,644,590 B2
(45) Date of Patent: Feb. 4, 2014

(54) METHOD OF MEASURING MEASUREMENT TARGET

(75) Inventors: Joong-Ki Jeong, Seoul (KR); Min-Young Kim, Seoul (KR); Hee-Wook You, Anyang-si (KR)

(73) Assignee: Koh Young Technology Inc., Seoul (KR)

( * ) Notice: Subject to any disclaimer, the term of this patent is extended or adjusted under 35 U.S.C. 154(b) by 0 days.

(21) Appl. No.: 13/619,161

(22) Filed: Sep. 14, 2012

(65) Prior Publication Data

US 2013/0010102 A1    Jan. 10, 2013

Related U.S. Application Data

(62) Division of application No. 12/779,599, filed on May 13, 2010.

(30) Foreign Application Priority Data

May 13, 2009 (KR) .......... 10-2009-0041514
Apr. 14, 2010 (KR) .......... 10-2010-0034057
May 11, 2010 (KR) .......... 10-2010-0043731

(51) Int. Cl.
*G06K 9/00* (2006.01)
*G06T 1/00* (2006.01)
*G01J 3/50* (2006.01)

(52) U.S. Cl.
CPC ...... *G06T 1/0007* (2013.01); *G01J 3/50* (2013.01)
USPC .............................. 382/145; 382/150; 348/93

(58) Field of Classification Search
None
See application file for complete search history.

(56) References Cited

U.S. PATENT DOCUMENTS 6,529,624 B1 * 3/2003 Kim .................. 382/150
2009/0252410 A1 * 10/2009 Chu Ke ............ 382/167

FOREIGN PATENT DOCUMENTS

| CN | 1659592     | 8/2005 |
| CN | 10-1150733  | 3/2008 |
| JP | 02-013802   | 1/1990 |
| JP | 06-160037   | 6/1994 |
| JP | 09-127007   | 5/1997 |
| JP | 10-066100   | 3/1998 |
| JP | 2004-037222 | 2/2004 |
| JP | 2004-198129 | 7/2004 |
| JP | 2005-172640 | 6/2005 |

* cited by examiner

*Primary Examiner* — Ryan Zeender
*Assistant Examiner* — Denisse Ortiz Roman
(74) *Attorney, Agent, or Firm* — Kile Park Reed & Houtteman PLLC

(57) ABSTRACT

In order to measure a measurement target on a PCB, height information of the PCB is acquired by using a first image photographed by illuminating a grating pattern light onto the PCB. Then, a first area protruding on the PCB by greater than a reference height is determined as the measurement target by using the height information. Thereafter, color information of the PCB is acquired by using a second image photographed by illuminating light onto the PCB. Then, the first color information of the first area determined as the measurement target out of the color information of the PCB is set as reference color information. Thereafter, the reference color information is compared with color information of an area except for the first area to judge whether the measurement target is formed in the area except for the first area. Thus, the measurement target may be accurately measured.

10 Claims, 10 Drawing Sheets

METHOD OF MEASURING MEASUREMENT TARGET

CROSS REFERENCE TO RELATED APPLICATION

This application is a divisional application of U.S. patent application Ser. No. 12/779,599, filed on May 13, 2010 (now pending), which claims priority to and the benefit of Korean Patent Applications No. 10-2009-0041514 filed on May 13, 2009, No. 10-2010-0034057 filed on Apr. 14, 2010, and No. 10-2010-0043731 filed on May 11, 2010, which are hereby incorporated by reference for all purposes as if fully set forth herein.

BACKGROUND OF THE INVENTION

1. Field of the Invention

Exemplary embodiments of the present invention relate to a method of measuring a measurement target. More particularly, exemplary embodiments of the present invention relate to a method of measuring a measurement target capable of enhancing accuracy.

2. Discussion of the Background

Generally, at least one printed circuit board (PCB) is employed in an electronic device. The PCB typically includes a base board, a connection pad part, and a driver chip electrically connected to the connection pad part.

A connection terminal is disposed beneath the driver chip to be electrically connected to the connection pad part, and the connection terminal is typically electrically connected to the connection pad part via solder formed on the connection pad part. Thus, a method of manufacturing the PCB necessarily includes forming the solder on the connection pad part.

An amount of the solder formed on the connection pad part may have an effect on electrical connection between the connection pad part and the connection terminal. That is, when the solder is formed too much, shorting defect may be generated between adjacent connection pad parts, and when the solder is formed relatively little, electrical bad connection may be generated between the connection pad part and the connection terminal.

As described above, since the amount of the solder formed on the connection pad part may have a great effect on electrical connection between the connection pad part and the connection terminal, a process of accurately measuring a volume of the solder formed on the PCB is required.

SUMMARY OF THE INVENTION

Exemplary embodiments of the present invention provide a method of measuring a measurement target capable of accurately measuring an area of the measurement target.

Exemplary embodiments of the present invention also provide a method of measuring a solder area capable of accurately measuring an area of solder formed on a printed circuit board.

Exemplary embodiments of the present invention also provide a method of correcting uniformity for each color before measuring a solder area for each color to increase accuracy of measuring the solder area.

Additional features of the invention will be set forth in the description which follows, and in part will be apparent from the description, or may be learned by practice of the invention.

An exemplary embodiment of the present invention discloses a method of measuring a measurement target on a printed circuit board (PCB). The method includes acquiring a three dimensional height information of the PCB by using a first image that is photographed by illuminating a grating pattern light using a first illumination unit onto the PCB, determining a first area protruding on the PCB by a height greater than or equal to a reference height as a measurement target by using the acquired height information, acquiring a color information of the PCB by using a second image that is photographed by illuminating a light generated from a second illumination unit onto the PCB, setting the first color information of the first area that is determined as the measurement target out of the acquired color information of the PCB as a reference color information, and comparing the reference color information with a color information of an area except for the first area to judge whether the measurement target is formed or not in the area except for the first area.

The method may further include classifying the reference color information of the first area and the color information of the area except for the first area into first and second clusters. Comparing the reference color information with the color information of the area except for the first area to judge whether the measurement target is formed or not in the area except for the first area may include checking whether the second cluster belongs to the first cluster or not, and in case that the second cluster belongs the first cluster, judging that an area corresponding to the second cluster belongs to the measurement target area.

The first and second clusters may include a feature extracted from the acquired color information by using a color coordinate system, and the feature includes at least one of hue, saturation, and intensity.

The method may further include acquiring a second color information of a second area, in which a predetermined comparison object is located to protrude on the PCB, from the measured color information of the PCB, acquiring a third color information of a third area, in which the measurement target is not formed, from the measured color information of the PCB, and classifying the first, second and third color informations of the first, second and third areas into first, second and third clusters, respectively, Comparing the reference color information with the color information of the area except for the first area to judge whether the measurement target is formed or not in the area except for the first area may include checking whether a color information of a predetermined portion on the PCB except for the first, second and third areas belongs to the first cluster, and in case that the color information belongs to the first cluster, judging that the measurement target is formed on the predetermined portion.

The method may further include acquiring a visibility information based on N grating pattern lights according to movement of a grating unit, and comparing a visibility information of the first area and a visibility information of an area except for the first area to judge whether the measurement target is formed or not in the area except for the first area.

Another exemplary embodiment of the present invention discloses a method of measuring a measurement target on a PCB. The method includes acquiring a three dimensional height information and a visibility information of the PCB by using a first image that is photographed by illuminating a grating pattern light using a first illumination unit onto the PCB, determining a first area protruding on the PCB by a height greater than or equal to a reference height as a measurement target by using the acquired height information, and comparing a first visibility information of the first area with a second visibility information of an area except for the first area to judge whether the measurement target is formed or not in the area except for the first area.

Still another exemplary embodiment of the present invention discloses a method of measuring a solder area. The method includes illuminating a plurality of color illuminations onto a PCB to acquire a plurality of color images, generating a saturation map by using the acquired color images, and extracting a solder area by using the saturation map.

Illuminating the color illuminations onto the PCB to acquire the color images may include illuminating a red illumination, a green illumination and a blue illumination to acquire a red image, a green image and a blue image, respectively.

Generating the saturation map by using the acquired color images may include acquiring at least one of hue information, saturation information and intensity information for each color through a color coordinate conversion of the color images, and generating the saturation map by using the saturation information for each color.

Extracting the solder area by using the saturation map may include excluding at least one of a wiring pattern area and a dark solder resist area from the saturation map by using the intensity information for each color and setting the solder area.

Extracting the solder area by using the saturation map may include producing a saturation average for each color in the solder area, generating a variance map by using the saturation information for each color and the saturation average for each color, and comparing a variance value in the variance map with a critical value to generate a solder map representing the solder area in which a solder is formed. Each of the variance values for pixels may be acquired by the equation, "variance value for each pixel=abs(R−RA)+abs(G−GA)+abs(B−BA)". 'R', 'G' and 'B' are saturation informations for each pixel, and 'RA', 'GA' and 'BA' are saturation averages for each color.

Before illuminating the color illuminations onto the PCB to acquire the color images, the method may include illuminating the color illuminations onto a target to acquire a plurality of illumination images for colors, obtaining an intensity for each pixel with respect to each of the illumination images for colors, and setting a compensation ratio for each color, corresponding to a ratio between the intensity for each pixel and an arbitrary reference intensity, for each pixel. Before generating the saturation map by using the acquired color images, the method may include compensating for the color images by using the compensation ratio for each color. The reference intensity may correspond to an average intensity of each of the color images.

Before illuminating the color illuminations onto the PCB to acquire the color images, the method may include illuminating the color illuminations onto a solder formed on the PCB to acquire a plurality of solder images for each color, obtaining an intensity for each color of the solder from each of the solder images for each color, and setting a compensation ratio for each color of the solder, corresponding to a ratio between the intensity for each color of the solder and an arbitrary reference intensity. Before generating the saturation map by using the acquired color images, the method may include compensating for the color images by using the compensation ratio for each color of the solder. The reference intensity may correspond to an average intensity of a plurality of solder intensities for each color.

Before illuminating the color illuminations onto the PCB to acquire the color images, the method may include setting a compensation ratio for each color of the color illuminations to correct color uniformity for the color illuminations, and setting a compensation ratio for each color of a solder to correct solder uniformity for the color illuminations. Before generating the saturation map by using the acquired color images, the method may include multiplying each color image by the compensation ratio for each color of the color illuminations and the compensation ratio for each color of the solder.

According to the above, an area corresponding to a height greater than or equal to a predetermined reference height H1 is determined as a solder area, and a color information of the solder area is set as a reference color information to compare the color information of the solder area with other area. Thus, an area corresponding to a height below the reference height H1, which may be omitted, is incorporated in the solder area, to thereby accurately measure the solder area.

In addition, even though solder is spread thin on the base board, which often generates in forming solder, the solder area may be measured with accuracy.

In addition, when the color information of the first area AR1, a solder area corresponding to a height greater than or equal to a predetermined reference height H1 and the color information of the second and third areas AR2 and AR3 are acquired and clustered, a portion not clear to incorporate in the solder area may be more clearly judged.

In addition, a solder area may be more accurately determined by using a visibility information.

In addition, a solder area may be more accurately determined by illuminating grating pattern lights in various directions.

In addition, a shape is three dimensionally measured and an area is two dimensionally judged with accuracy, and an area may be three dimensionally and two dimensionally determined in real-time, so that effects according to equipments such as illuminations or a condition of a PCB may be reduced, and robustness for noise may be attained.

In addition, the saturation map and the variance map are generated by using the color images obtained through the color illuminations, and the solder area is set by using the saturation map and the variance map, thereby increasing accuracy of measuring the solder area. In addition, before measuring the solder area, at least one process of correcting the color uniformity for the color illuminations and correcting the solder uniformity for the color illuminations is performed, thereby enhancing accuracy of measuring the solder area.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
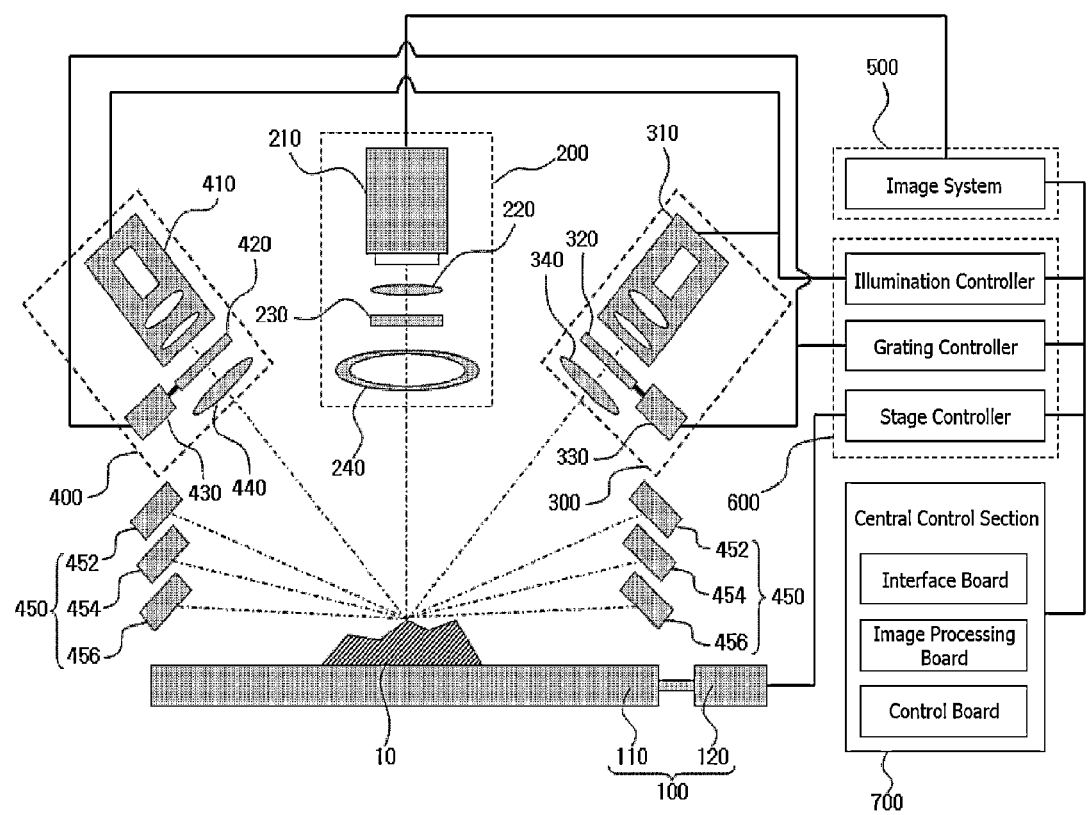
FIG. 1 is a schematic view illustrating a three dimensional shape measurement apparatus used to a method of measuring a three dimensional shape according to an exemplary embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

FIG. 1 is a schematic view illustrating a three dimensional shape measurement apparatus used to a method of measuring a three dimensional shape according to an exemplary embodiment of the present invention.

Referring to FIG. 1, a three dimensional shape measurement apparatus used to a method of measuring a three dimensional shape according to an exemplary embodiment of the present invention may include a measurement stage section 100, an image photographing section 200, a first illumination unit including first and second illumination sections 300 and 400, a second illumination unit 450, an image acquiring section 500, a module control section 600 and a central control section 700.

The measurement stage section 100 may include a stage 110 supporting a measurement target 10 and a stage transfer unit 120 transferring the stage 110. In an exemplary embodiment, according as the measurement target 10 moves with respect to the image photographing section 200 and the first and second illumination sections 300 and 400 by the stage 110, a measurement location may be changed in the measurement target 10.

The image photographing section 200 is disposed over the stage 110 to receive light reflected by the measurement target 10 and measure an image of the measurement target 10. That is, the image photographing section 200 receives the light that exits the first and second illumination sections 300 and 400 and is reflected by the measurement target 10, and photographs a plan image of the measurement target 10.

The image photographing section 200 may include a camera 210, an imaging lens 220, a filter 230 and a lamp 240. The camera 210 receives the light reflected by the measurement target 10 and photographs the plan image of the measurement target 10. The camera 210 may include, for example, one of a CCD camera and a CMOS camera. The imaging lens 220 is disposed under the camera 210 to image the light reflected by the measurement target 10 on the camera 210. The filter 230 is disposed under the imaging lens 220 to filter the light reflected by the measurement target 10 and provide the filtered light to the imaging lens 220. The filter 230 may include, for example, one of a frequency filter, a color filter and a light intensity control filter. The lamp 240 may be disposed under the filter 230 in a circular shape to provide the light to the measurement target 10, so as to photograph a particular image such as a two-dimensional shape of the measurement target 10.

The first illumination section 300 may be disposed, for example, at a right side of the image photographing section 200 to be inclined with respect to the stage 110 supporting the measurement target 10. The first illumination section 300 may include a first light source unit 310, a first grating unit 320, a first grating transfer unit 330 and a first condensing lens 340. The first light source unit 310 may include a light source and at least one lens to generate light, and the first grating unit 320 is disposed under the first light source unit 310 to change the light generated by the first light source unit 310 into a first grating pattern light having a grating pattern. The first grating transfer unit 330 is connected to the first grating unit 320 to transfer the first grating unit 320, and may include, for example, one of a piezoelectric transfer unit and a fine linear transfer unit. The first condensing lens 340 is disposed under the first grating unit 320 to condense the first grating pattern light exiting the first grating unit 320 on the measurement target 10.

For example, the second illumination section 400 may be disposed at a left side of the image photographing section 200 to be inclined with respect to the stage 110 supporting the measurement target 10. The second illumination section 400 may include a second light source unit 410, a second grating unit 420, a second grating transfer unit 430 and a second condensing lens 440. The second illumination section 400 is substantially the same as the first illumination section 300 described above, and thus any further description will be omitted.

When the first grating transfer unit 330 sequentially moves the first grating unit 320 by N times and N first grating pattern lights are illuminated onto the measurement target 10 in the first illumination section 300, the image photographing section 200 may sequentially receive the N first grating pattern lights reflected by the measurement target 10 and photograph N first pattern images. In addition, when the second grating transfer unit 430 sequentially moves the second grating unit 420 by N times and N second grating pattern lights are illuminated onto the measurement target 10 in the second illumination section 400, the image photographing section 200 may sequentially receive the N second grating pattern lights reflected by the measurement target 10 and photograph N second pattern images. The 'N' is a natural number, and for example may be four.

In an exemplary embodiment, the first and second illumination sections 300 and 400 are described as an illumination apparatus generating the first and second grating pattern lights. Alternatively, the illumination section may be more than or equal to three. In other words, the grating pattern light may be illuminated onto the measurement target 10 in various directions, and various pattern images may be photographed. For example, when three illumination sections are disposed in an equilateral triangle form with the image photographing section 200 being the center of the equilateral triangle form, three grating pattern lights may be illuminated onto the measurement target 10 in different directions. For example, when four illumination sections are disposed in a square form with the image photographing section 200 being the center of the square form, four grating pattern lights may be illuminated onto the measurement target 10 in different directions. In addition, the first illumination unit may include eight illumination sections, and grating pattern lights may be illuminated onto the measurement target 10 in eight directions to photograph an image.

The second illumination unit 450 illuminates light for acquiring a two dimensional image of the measurement target 10 onto the measurement target 10. In an exemplary embodiment, the second illumination unit 450 may include a red illumination 452, a green illumination 454, and a blue illumination 456. For example, the red illumination 452, the green illumination 454, and the blue illumination 456 may be disposed in a circular shape over the measurement target 10 to illuminate a red light, a green light and a blue light, respectively, and may be disposed at different heights as shown in FIG. 1.

The image acquiring section 500 is electrically connected to the camera 210 of the image photographing section 200 to acquire the pattern images according to the first illumination unit from the camera 210 and store the acquired pattern images. In addition, the image acquiring section 500 acquires the two dimensional images according to the second illumination unit from the camera 210 and store the acquired two dimensional images. For example, the image acquiring section 500 may include an image system that receives the N first pattern images and the N second pattern images photographed in the camera 210 and stores the images.

The module control section 600 is electrically connected to the measurement stage section 100, the image photographing section 200, the first illumination section 300 and the second illumination section 400, to control the measurement stage section 100, the image photographing section 200, the first illumination section 300 and the second illumination section 400. The module control section 600 may include, for example, an illumination controller, a grating controller and a stage controller. The illumination controller controls the first and second light source units 310 and 410 to generate light, and the grating controller controls the first and second grating transfer units 330 and 430 to move the first and second grating units 320 and 420. The stage controller controls the stage transfer unit 120 to move the stage 110 in an up-and-down motion and a left-and-right motion.

The central control section 700 is electrically connected to the image acquiring section 500 and the module control section 600 to control the image acquiring section 500 and the module control section 600. Particularly, the central control section 700 receives the N first pattern images and the N second pattern images from the image system of the image acquiring section 500 to process the images, so that three dimensional shape of the measurement target may be measured. In addition, the central control section 700 may control a illumination controller, a grating controller and a stage controller of the module control section 600. Thus, the central control section may include an image processing board, a control board and an interface board.

Hereinafter, a method of measuring the measurement target 10 formed on a printed circuit board by using the above described three dimensional shape measurement apparatus will be described in detail. It will be described employing a solder as an example of the measurement target 10.

Figure 2:
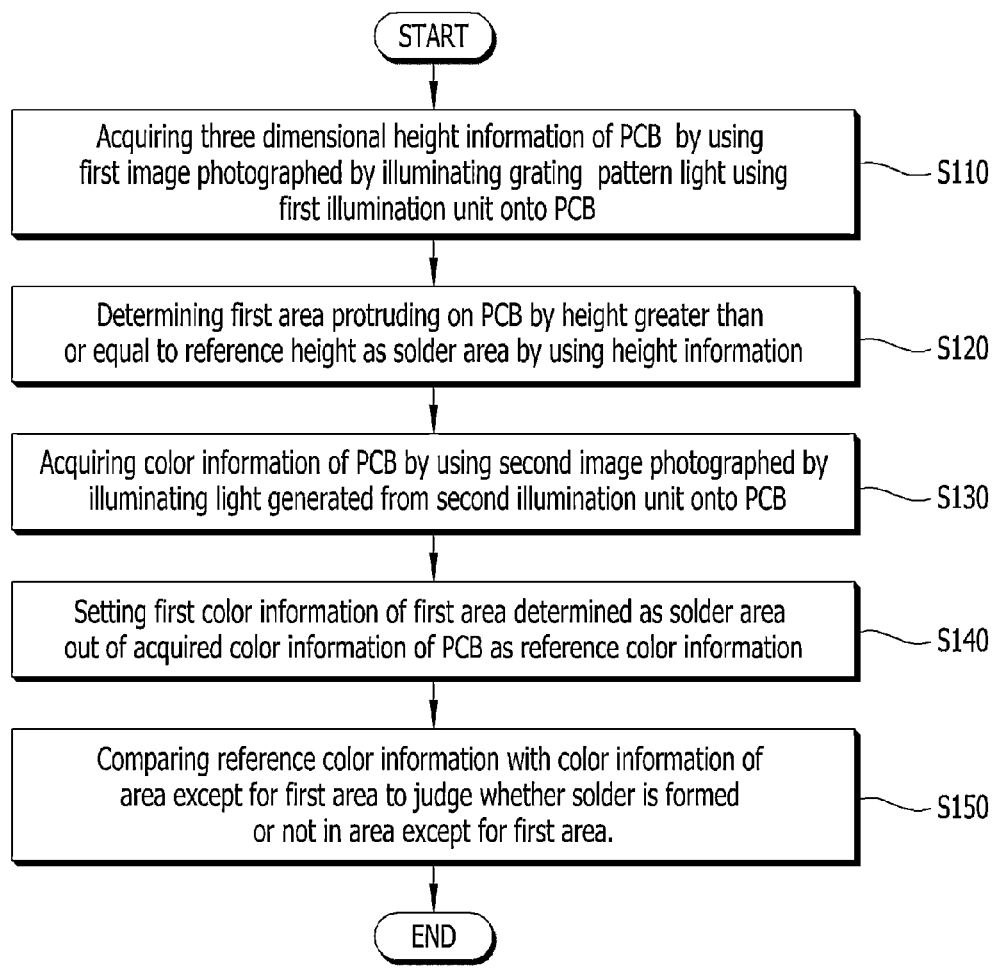
FIG. 2 is a flow chart showing a method of measuring a solder area according to an exemplary embodiment of the present invention.
Figure 3:
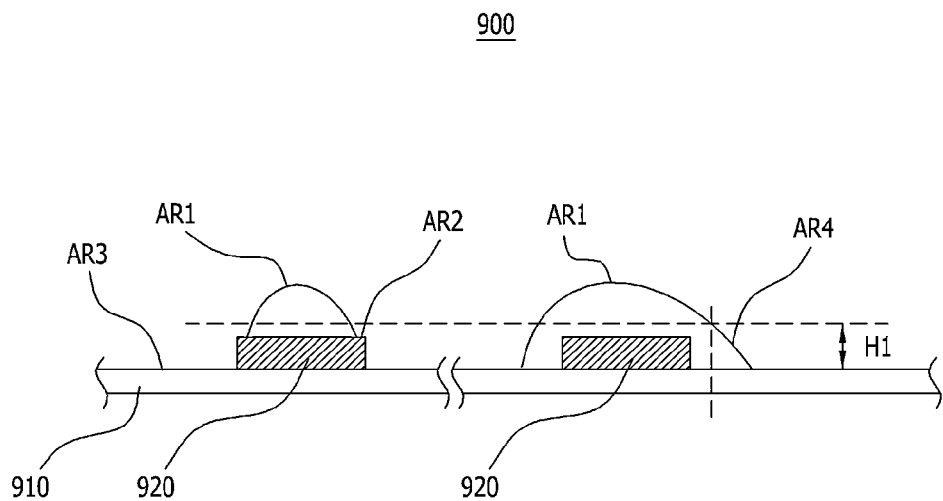
FIG. 3 is a cross-sectional view illustrating a portion of a PCB on which a solder is formed.

FIG. 2 is a flow chart showing a method of measuring a solder area according to an exemplary embodiment of the present invention. FIG. 3 is a cross-sectional view illustrating a portion of a PCB on which a solder is formed.

Referring to FIGS. 1 to 3, in order to measure a solder area, firstly, a three dimensional height information of the PCB 900 is acquired by using a first image that is photographed by illuminating a grating pattern light using a first illumination unit onto the PCB 900 in step S1110. For example, the grating pattern light may be illuminated in at least two directions.

The three dimensional height information may be acquired by performing a bucket algorithm with respect to the first image that is acquired by illuminating grating pattern lights according to sequential movement by N times of the first and second grating units 320 and 420.

Then, a first area AR1 protruding on a base board 910 of the PCB 900 by a height greater than or equal to a reference height H1 is determined as a solder area by using the acquired height information in step S1120.

When an area corresponding to a height greater than or equal to a predetermined minimum height threshold may be generally regarded as a solder area, the reference height H1 may be set as the predetermined minimum height threshold.

Thereafter, a color information of the PCB 900 is acquired by using a second image that is photographed by illuminating a light generated from a second illumination unit 450 onto the PCB 900 in step S1130.

The second illumination unit 450 generates a light for acquiring a two dimensional image of the measurement target 10. In an exemplary embodiment, the second illumination unit 450 may include a red illumination 452, a green illumination 454 and a blue illumination 456 generating a red light, a green light and a blue light, respectively. The second image may be acquired using not only a color camera, but also a black and white camera. Thus, the camera 210 as shown in FIG. 1 may include a black and white camera. In another exemplary embodiment, the second illumination unit 250 may include an illumination unit of a monochromatic light. The second image may be acquired using a color camera, and the camera 210 as shown in FIG. 1 may include a color camera.

The color information may include, for example, RGB (red, green and blue) information or CMY (cyan, magenta and yellow) information. Besides, the first color information may include a color information according to other color combination. The first color information may be acquired by a pixel unit of the first area AR1.

Meanwhile, the color information of the PCB 900 may be acquired as follows.

Figure 4:
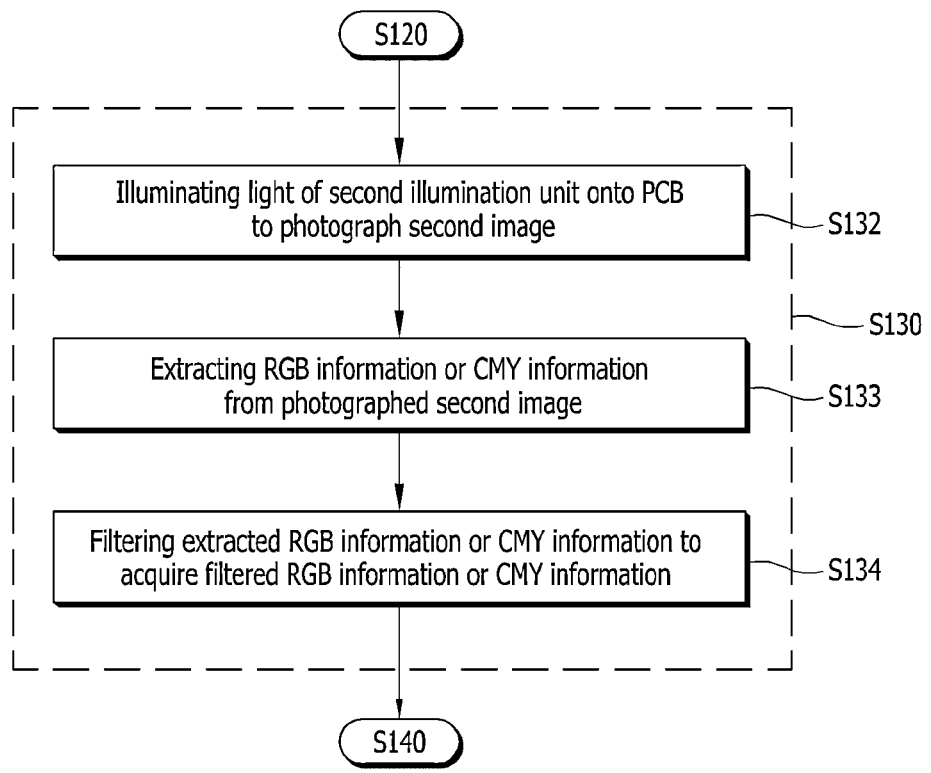
FIG. 4 is a flow chart showing an exemplary embodiment of a process of acquiring two dimensional color information included in the method of measuring the solder area in FIG. 2.

FIG. 4 is a flow chart showing an exemplary embodiment of a process of acquiring two dimensional color information included in the method of measuring the solder area in FIG. 2.

Referring to FIG. 4, in order to acquire the color information of the PCB 900, firstly, the light generated from the second illumination unit 450 is illuminated onto the PCB 900 to photograph the second image in step S1132.

Then, the RGB information or the CMY information is extracted from the photographed second image in step S1133. In an exemplary embodiment, after the photographed second image is acquired by the image acquiring section 500 shown in FIG. 1, the RGB information or the CMY information may be extracted by using the image processing board shown in FIG. 1.

Thereafter, the extracted RGB information or CMY information is filtered to acquire the filtered RGB information or CMY information in step S1134. In an exemplary embodiment, in the image processing board, data deviating from an average is excluded from the extracted RGB information or CMY information by a selected criterion, and remaining data except the deviating data is finally determined as the RGB information or the CMY information.

Referring again to FIGS. 1 to 3, then, a first color information of the first area AR1 that is determined as a solder area out of the acquired color information of the PCB 900 is set as a reference color information in step S1140.

Thereafter, the reference color information and a color information of an area except for the first area AR1 are compared to judge whether the solder is formed or not in the area except for the first area AR1 in step S1150.

Meanwhile, in order to acquire an area having a color information that is substantially the same as the reference color information, color information of other areas may be used.

Figure 5:
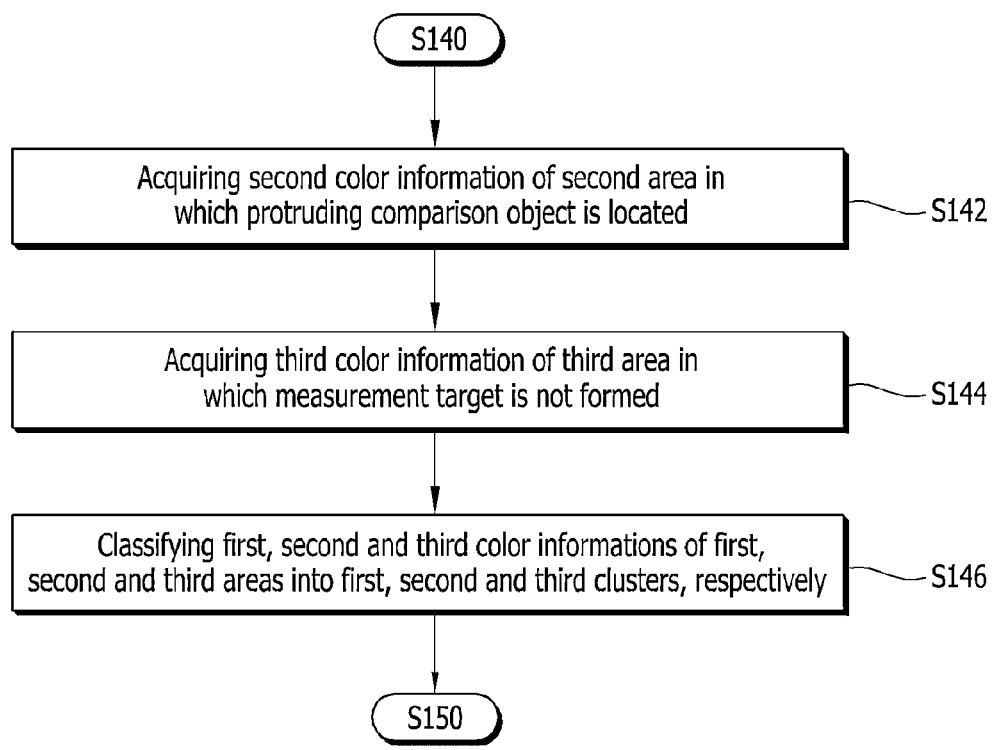
FIG. 5 is a flow chart showing a method of measuring a solder area according to another exemplary embodiment of the present invention.

FIG. 5 is a flow chart showing a method of measuring a solder area according to another exemplary embodiment of the present invention.

Referring to FIGS. 3 and 5, after setting the first color information of the first area AR1 as the reference color information in step S1140, a second color information of a second area AR2 in which a predetermined protruding comparison object 920 is located is acquired from the measured color information of the PCB 900 in step S1142. The comparison object 920 may correspond to a pad of the PCB.

Since the second color information of the second area AR2 may be acquired from the color information, the second color information may be substantially the same form as the first color information. The second color information may include an RGB information or a CMY information. Besides, the second color information may include a color information according to other color combination.

Thereafter, a third color information of a third area AR3 in which a measurement target is not formed is acquired from the measured color information of the PCB 900 in step S1144. The third area AR3 corresponds to a surface area having no height.

Since the third color information of the third area AR3 may be acquired from the color information, the third color information may have substantially the same form as the first color information and the second color information. For example, the third color information may include an RGB information or a CMY information. Besides, the third color information may include a color information according to other color combination.

Then, the first, second and third color informations of the first, second and third areas AR1, AR2 and AR3 are classified into first, second and third clusters in step S1146.

The first, second and third color informations indicate color information of each area, and the color information shows a characteristic tendency for each area. Thus, the first, second and third color informations may form a specific cluster for each area.

The cluster may include a feature extracted from the acquired color information by using a color coordinate system. For example, the first, second and third cluster may include at least one of hue, saturation and intensity (HSI) converted from the RGB information or the CMY information. The process of converting the RGB information or the CMY information into the HSI information may be performed by using well-known methods, and thus any further description will be omitted.

A clustering algorithm may be applied to the first, second and third areas AR1, AR2 and AR3 with at least one information of each HSI information of the areas, so that the first, second and third areas AR1, AR2 and AR3 may be classified into the first, second and third clusters, respectively.

As described above, after the first, second and third areas AR1, AR2 and AR3 are classified into the clusters according to the color information, in comparing the reference color information and the color information of the area except for the first area AR1 to judge whether the solder is formed or not in the area except for the first area AR1 in step S1150, it is checked whether a color information of a predetermined portion of the PCB 900 except for the first, second and third areas AR1, AR2 and AR3 belongs to the first cluster or not, and in case that the color information belongs to the first cluster, it may be judged that the solder is formed on the predetermined portion.

In case that a predetermined portion on the base board 910, which does not belong to the first, second and third areas AR1, AR2 and AR3, corresponds to an area AR4 of a solder existing below the reference height H1 (hereinafter, referred to as "fourth area"), since a color information of the fourth area AR4 is similar to the first color information of the first area AR1, the fourth area AR4 belongs to a group that is the same as the group of the first area AR1 classified into the first cluster according to the first color information. That is, the fourth area AR4 may be classified into the first cluster, which is like the first area AR1.

Accordingly, in comparison with a method of judging an area only corresponding to a height greater than or equal to a predetermined reference height as a solder area, an area corresponding to a height smaller than the predetermined reference height as a solder area may be also included in the solder area, so that the solder area may be more correctly determined.

Although an example of classifying areas into three clusters is described in FIG. 5, the number of the clusters may be two or greater than or equal to four.

For example, when the number of the clusters is four, the solder area may be determined as follows.

Firstly, a color information of a predetermined area except for the first area AR1 determined as the solder area is acquired to classify the reference color information of the first area AR1 and the color information of the predetermined area into first and second clusters, respectively. Then, in comparing the reference color information and the color information of the area except for the first area AR1 to judge whether the solder is formed or not in the area except for the first area AR1 in step S1150, it is checked whether the second cluster belongs to the first cluster or not, and in case that the second cluster belongs to the first cluster, it may be judged that the area corresponding to the second cluster belongs to the solder area.

In acquiring the color information of the PCB 900 in step S1130, a visibility information may be additionally used. The visibility represents a ratio of amplitude $B_i(x,y)$ to average $A_i(x,y)$ in brightness signals of an image, and roughly has a tendency to increase as reflectivity increases. The visibility $V_i(x,y)$ is defined as follows.

$$V_i(x,y) = B_i(x,y)/A_i(x,y)$$

The grating pattern light is illuminated onto the PCB 900 in various directions to photograph various sorts of pattern images. As shown in FIG. 1, the image acquiring section 500 extracts N brightness degrees $I^i_1, I^i_2, \ldots, I^i_N$ at each position i(x,y) in an X-Y coordinate system from N pattern images photographed in the camera 210, and produces average brightness $A_i(x,y)$ and visibility $V_i(x,y)$ by using an N-bucket algorithm.

For example, when N is 3, and N is 4, the visibility may be produced as follows.

When N is 3, the visibility is produced as follows.

$$A_i(x, y) = \frac{I^i_1 + I^i_2 + I^i_3}{3}$$

$$V_i(x, y) = \frac{B_i}{A_i} = \frac{\sqrt{(2I^i_1 - I^i_2 - I^i_3)^2 + 3(I^i_2 - I^i_3)^2}}{(I^i_1 + I^i_2 + I^i_3)}$$

When N is 4, the visibility is produced as follows.

$$A_i(x, y) = \frac{I^i_1 + I^i_2 + I^i_3 + I^i_4}{4}$$

$$V_i(x, y) = \frac{B_i}{A_i} = \frac{2\sqrt{(I^i_1 - I^i_3)^2 + (I^i_2 - I^i_4)^2}}{(I^i_1 + I^i_2 + I^i_3 + I^i_4)}$$

The color informations such as the first, second and third color informations described above show a characteristic tendency for each area, and in addition, the visibility information produced as above also shows a characteristic tendency for each area. Thus, in addition to the color information, the visibility information may be optionally used to measure the solder area. Also, the visibility information only may be used to measure the solder area without the color information.

Particularly, the visibility information may be acquired based on N grating pattern lights according to the movement of the grating unit, and then the visibility information for the first area and the visibility information for the area except for the first area are compared to judge whether the measurement target is formed or not in the area except for the first area.

The visibility information of the PCB may be acquired by using the first image described in FIG. 2. That is, since the first image includes all the information for acquiring the visibility information described above, the visibility information may be acquired from the first image.

The first, second and third areas AR1, AR2 and AR3 may be classified into the first, second and third clusters, which is described in FIG. 5, by using the acquired visibility information, and thus it may be judged whether a predetermined portion of the base board 910 except for the first, second and third areas AR1, AR2 and AR3 belongs the first cluster or not.

After determining the solder area as described above, the determined solder area may be used in various methods. For example, volume of the area determined as the solder area is produced, and it may be judged whether the PCB on which the solder formed is good or bad by using the produced volume.

As described above, an area corresponding to a height greater than or equal to a predetermined reference height H1 is determined as a solder area, and a color information of the solder area is set as a reference color information to compare the color information of the solder area with other area. Thus, an area corresponding to a height below the reference height H1, which may be omitted, is incorporated in the solder area, to thereby accurately measure the solder area.

In addition, even though solder is spread thin on the base board, which often generates in forming solder, the solder area may be measured with accuracy.

In addition, when the color information of the first area AR1, a solder area corresponding to a height greater than or equal to a predetermined reference height H1 and the color information of the second and third areas AR2 and AR3 are acquired and clustered, a portion not clear to incorporate in the solder area may be more clearly judged.

In addition, a solder area may be more accurately determined by using a visibility information.

In addition, a solder area may be more accurately determined by illuminating grating pattern lights in various directions.

In addition, a shape is three dimensionally measured and an area is two dimensionally judged with accuracy, and an area may be three dimensionally and two dimensionally determined in real-time, so that effects according to equipments such as illuminations or a condition of a PCB may be reduced, and robustness for noise may be attained.

Figure 6:
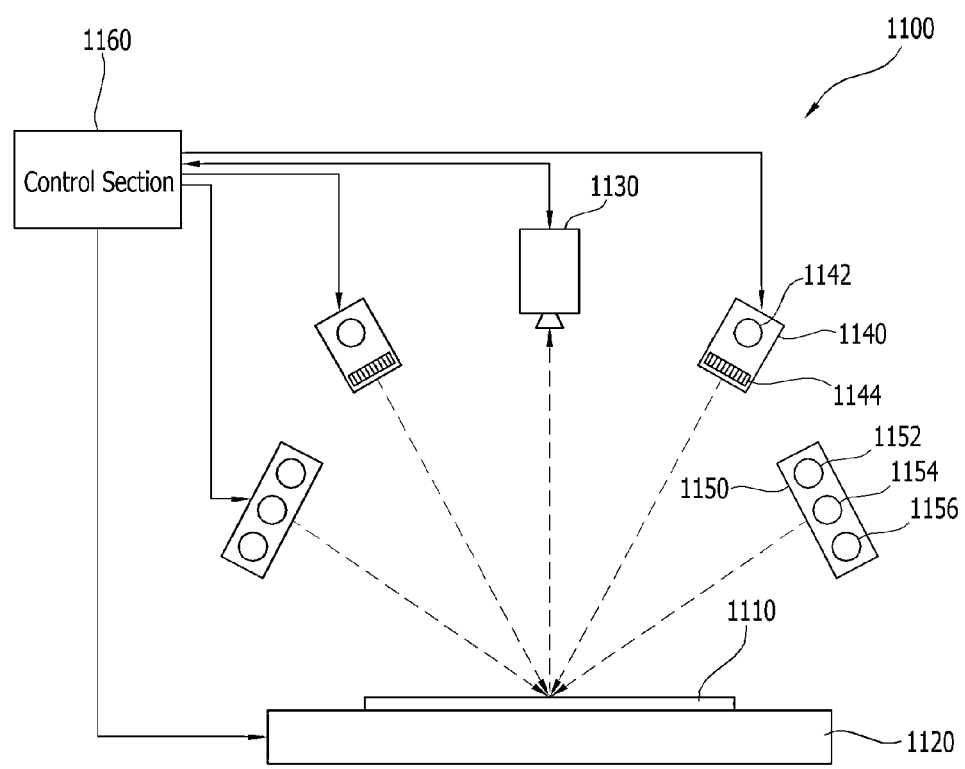
FIG. 6 is a schematic view illustrating a three dimensional shape measurement apparatus used to a method of measuring a three dimensional shape according to another exemplary embodiment of the present invention.

FIG. 6 is a schematic view illustrating a three dimensional shape measurement apparatus used to a method of measuring a three dimensional shape according to another exemplary embodiment of the present invention.

Referring to FIG. 6, a three dimensional shape measurement apparatus 1100 used to a method of measuring a three dimensional shape according to an exemplary embodiment of the present invention may include a stage 1120, an image photographing section 1130, a first illumination unit 1140, a second illumination unit 1150 and a control section 1160.

The stage 1120 supports a measurement target 1110 such as a PCB, and moves according to control of the control section 1160 to transfer the measurement target 1110 to a measurement location. According as the measurement target 1110 moves with respect to the image photographing section 1130 and the first illumination unit 1140 by the stage 1120, the measurement location at the measurement target 1110 may be changed.

The image photographing section 1130 is installed over the stage 1120, and receives light reflected by the measurement target 1110 to photograph an image of the measurement target 1110. The image photographing section 1130 is installed, for example, over the stage 1110 in a direction substantially perpendicular to a reference surface of the stage 1120.

The image photographing section 1130 may include a camera and an imaging lens to photograph the image of the measurement target 1110. The camera receives the light reflected by the measurement target 1110 to photograph the image of the measurement target 1110, and may include, for example, a CCD camera or a CMOS camera. The imaging lens is disposed under the camera to image the light reflected by the measurement target 1110 on the camera.

The image photographing section 1130 receives a light reflected by the measurement target 1110, onto which a pattern illumination illuminated from a first illumination unit 1140 is incident, and photographs a pattern image of the measurement target 1110. In addition, the image photographing section 1130 receives a light reflected by the measurement target 1110, onto which a color illumination illuminated from a second illumination unit 1150 is incident, and photographs a color image of the measurement target 1110.

The first illumination unit 1140 is installed over the stage 1120 to be inclined with respect to the stage 1120 by a predetermined angle. The first illumination unit 1140 is for measuring a three dimensional shape of the measurement target 1110, and generates a pattern illumination to illuminate the measurement target 1110. For example, the first illumination unit 1140 illuminates the pattern illumination inclined by about 30 degrees with respect to a normal line of the reference surface of the stage 1120.

In order to increase measurement accuracy, the first illumination unit 1140 may be plural to illuminate the pattern illumination in various directions. A plurality of first illumination units 1140 may be disposed along a circumferential direction at substantially the same angle based on the center of the image photographing section 1130. For example, the three dimensional shape measurement apparatus 1100 may include six first illumination units 1140 spaced apart at about 60 degrees. Alternatively, the three dimensional shape measurement apparatus 1100 may include first illumination units 1140 of various numbers such as 2, 3, 4, 8, etc. The first illumination units 1140 illuminate the pattern illumination in different directions with respect to the measurement target 1110 at substantially the same time interval.

Each first illumination unit 1140 may include a light source 1142 and a grating element 1144 to generate the pattern illumination. The illumination generated from the light source 1142 is converted into the pattern illumination while passing through the grating element 1144. The grating element 1144 moves n times by $2\pi/n$ by using a grating transfer unit such as a piezoelectric (PZT) actuator to generate the phase transited pattern illumination. The "n" is a natural number of greater than or equal to 2. The first illumination unit 1140 illuminates the pattern illumination onto the measurement target 1110 for each movement while moving the grating element 1144 by n times. The first illumination unit 1140 may further include a projection lens (not shown) to focus the pattern illumination formed by the grating element 1144 and project the focused pattern illumination onto the measurement target 1110.

The second illumination unit 1150 is for acquiring a two dimensional image of the measurement target 1110, and generates and illuminates the color illumination onto the measurement target 1110. The second illumination unit 1150 may include a plurality of color illumination parts to generate different color illuminations. For example, the second illumination unit 1150 may include a red illumination part 1152 generating a red illumination, a green illumination part 1154 generating a green illumination and a blue illumination part 1156 generating a blue illumination. The red illumination part 1152, the green illumination part 1154 and the blue illumination part 1156 are disposed over the measurement target 1110 in a circular form to illuminate the red illumination, the green illumination and the blue illumination onto the measurement target 1110, respectively.

The control section 1160 totally controls the above described elements. Particularly, the control section 1160 controls the movement of the stage 1120 to dispose the measurement target 1110 at the measurement location. The control section 1160 operates the first illumination units 1140 sequentially. The control section 1160 moves the grating element 1144 of each first illumination unit 1140 by pitch and controls the first illumination unit 1140 to illuminate the pattern illumination onto the measurement target 1110 for each movement. The control section 1160 controls the second illumination unit 1150 to illuminate the color illumination onto the measurement target 1110, so as to acquire two dimensional image of the measurement target 1110. The control section 1160 controls the image photographing section 1130 to photograph the pattern image acquired by using the pattern illumination that is illuminated from the first illumination unit 1140 and reflected by the measurement target 1110, and to photograph the color image acquired by using the color illumination that is illuminated from the second illumination unit 1150 and reflected by the measurement target 1110. In addition, the control section 1160 measures the three dimensional shape of the measurement target 1110 by using the pattern image and the color image photographed in the image photographing section 1130.

Hereinafter, a method of measuring a solder area on a PCB by using the three dimensional shape measurement apparatus will be described.

Figure 7:
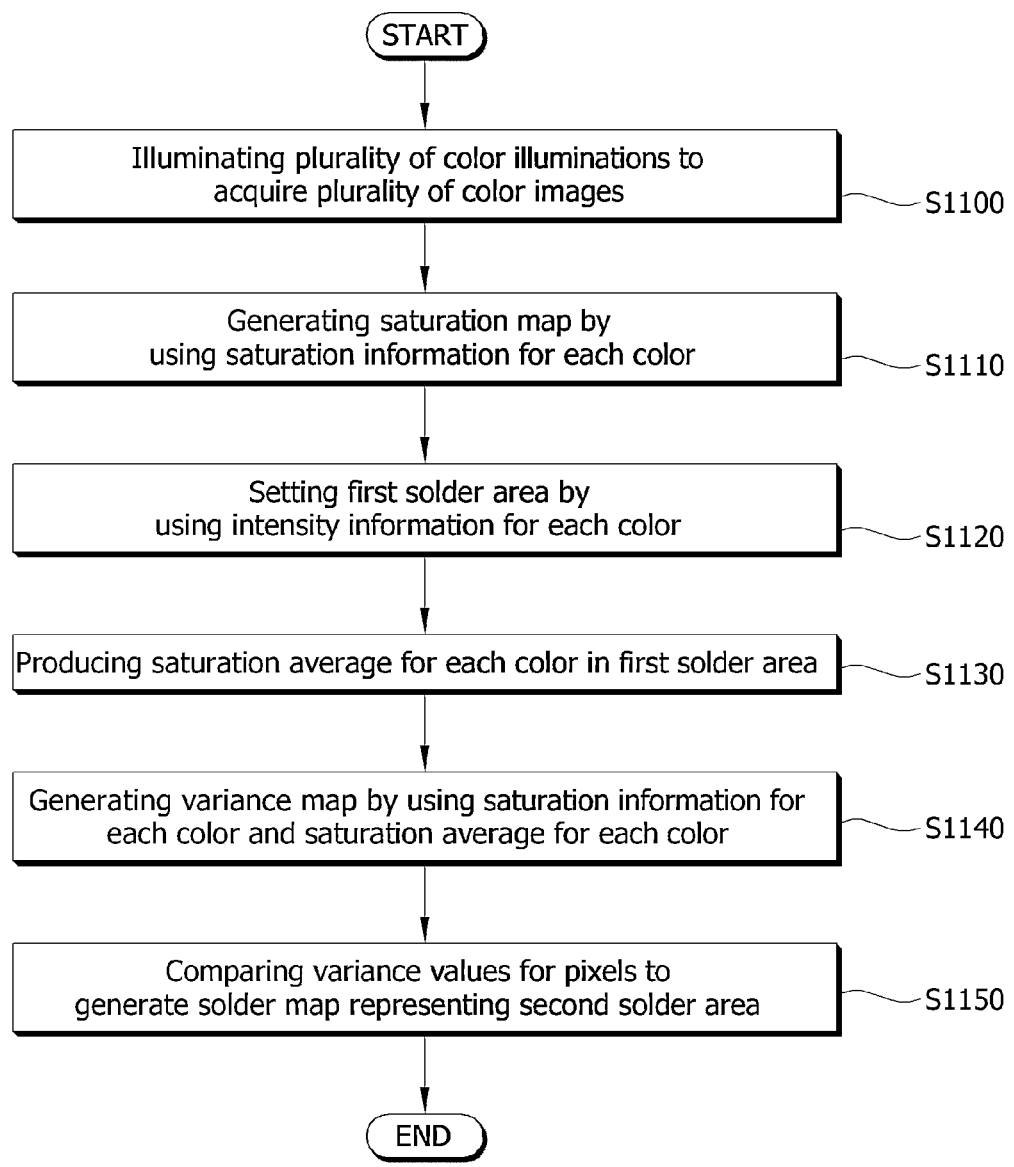
FIG. 7 is a flow chart showing a method of measuring a solder area according to still another exemplary embodiment of the present invention.

FIG. 7 is a flow chart showing a method of measuring a solder area according to still another exemplary embodiment of the present invention.

Referring to FIGS. 6 and 7, in order to measure a solder area on a PCB 1110, firstly, a plurality of color illuminations is illuminated onto the PCB 1110 to acquire a plurality of color images in step S1100. That is, after sequentially illuminating the color illuminations onto the PCB 1110 by using the second illumination unit 1150, the color image is acquired corresponding to each color illumination by using the image photographing section 1130. For example, after illuminating a red illumination, a green illumination and a blue illumination onto the PCB 1110 by using the red illumination part 1152, the green illumination part 1154 and the blue illumination part 1156 included in the second illumination unit 1150, a red image, a green image and a blue image are acquired corresponding to each color illumination.

Figure 8:
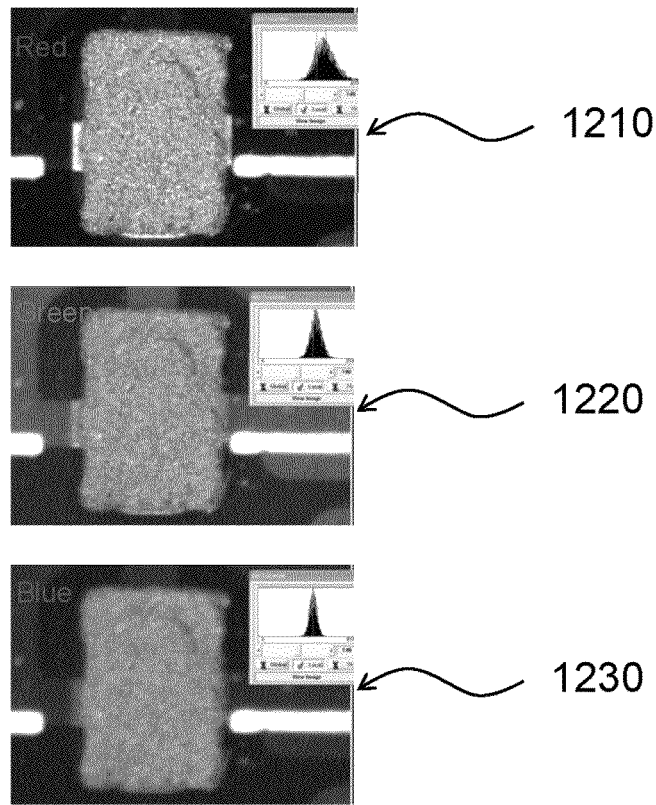
FIG. 8 shows a red image, a green image and a blue image corresponding to a red illumination, a green illumination and a blue illumination, respectively.

FIG. 8 shows a red image, a green image and a blue image corresponding to a red illumination, a green illumination and a blue illumination, respectively.

Referring to FIG. 8, it may be confirmed that distributions of a red image 1210, a green image 1220 and a blue image 1230 within a field of view (FOV) are different from each other due to chromatic aberration according to using the red illumination, the green illumination and the blue illumination having different wavelengths.

Then, an HSI information including hue, saturation and intensity for each color is acquired through the color coordinate conversion of the acquired color images. The process of converting an RGB information into the HSI information may be performed by using well-known methods, and thus any further description will be omitted.

Before color coordinate converting the acquired color images, the saturation may be relieved by applying an average filter to the acquired color images.

Figure 9:
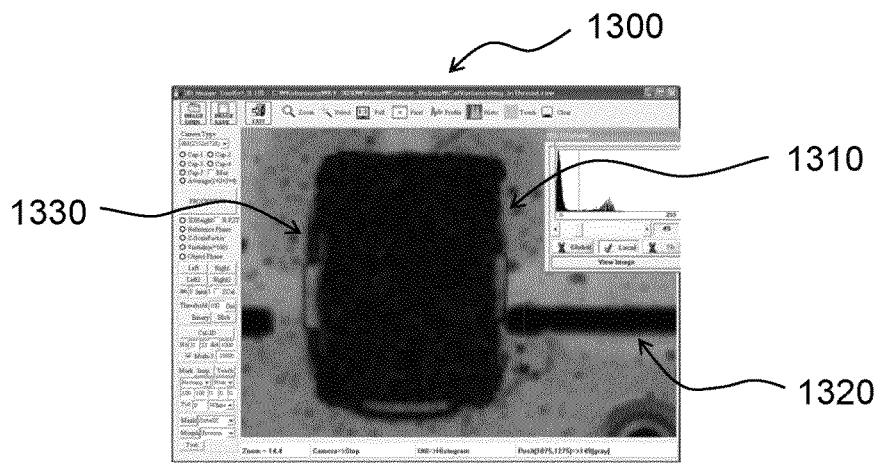
FIG. 9 is an image showing an example of a saturation map.

Thereafter, a saturation map 1300 is generated by using a saturation information for each color of the HSI information in step S1110. An example of the generated saturation map 1300 is shown in FIG. 9.

The saturation map 1300 may be generated by using the saturation information for each pixel with respect to the red image 1210, the green image 1220 and the blue image 1230. Particularly, the saturation map 1300 may be generated based on the saturation for each pixel produced by the following Equation 1.

$$\text{saturation} = (1 - 3 \cdot \text{Min}(R,G,B)/(R+G+B)) \quad \text{Equation 1}$$

In the Equation 1, 'IR' is a saturation information for each pixel in the red image 1210, 'G' is a saturation information for each pixel in the green image 1220, and 'B' is a saturation information for each pixel in the blue image 1230.

The saturation map 1300 generated from the Equation 1 has a range of about 0 to about 1, and represents a primary color as the saturation map 1300 becomes closer to 1. Since the solder 1310, typically, is close to achromatic color, an area having a value close to 0 in the saturation map 1300 may be primarily judged as the solder area.

Beside the solder 1310, however, since a wiring pattern 1320, a dark solder resist 1330, etc is also close to achromatic color, an area of the wiring pattern 1320, an area of the dark solder resist 1330, etc. in the saturation map 1300 may be mistaken for the solder area.

Accordingly, after generating the saturation map 1300, an unnecessary area such as the wiring pattern 1320, the dark solder resist 1330, etc. may be excluded from the saturation map 1300.

Thus, at least one of the area of wiring pattern 1320 and the area of the solder resist 1330 is excluded from the saturation map 1300 by using the intensity information for each color of the HSI information to set a first solder area in step S1120.

The first solder area may be set by using the intensity information out of the HSI information obtained by the color coordinate conversion of the color images. Particularly, among the solder 1310, the wiring pattern 1320 and the dark solder resist 1330, there may exist little difference in view of the saturation, but there may exist much difference in view of the intensity. That is, since the wiring pattern 1320 including metal has great reflectivity in comparison with the solder 1310, the intensity of the wiring pattern 1320 is detected greater than that of the solder 1310, and since the dark solder resist 1330 has little reflectivity in comparison with the solder 1310, the intensity of the dark solder resist 1330 is detected much less than that of the solder 1310. Thus, an area in which the intensity is great or little in comparison with the solder 1310 may be removed by using the difference of the intensity, to thereby remove the unnecessary area such as the wiring pattern 1320, the dark solder resist 1330, etc. from the saturation map 1300.

Then, a saturation average for each color in the first solder area is produced in step S1130. That is, the saturation average for each color is produced for each of the red image 1210, the green image 1220 and the blue image 1230 shown in FIG. 8 based on the set first solder area. Since the produced saturation average for each color corresponds to the saturation average for the first solder area in which it is judged that the solder 1310 is substantially formed, the produced saturation average may be regarded as a criterion for the saturation of the solder 1310.

Figure 10:
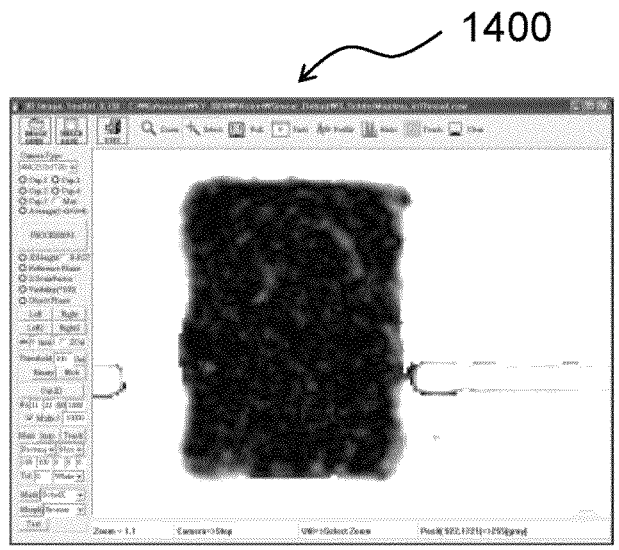
FIG. 10 is an image showing an example of a variance map.

Thereafter, a variance map 1400 is generated by using the saturation information for each color and the saturation average for each color in step S1140. An example of the generated variance map 1400 is shown in FIG. 10.

The variance map 1400 may be generated by using the saturation information for each pixel of the red image 1210, the green image 1220 and the blue image 1230 and the saturation average for each color of the red image 1210, the green image 1220 and the blue image 1230. Particularly, the variance map 1400 may be generated based on a variance value for each pixel produced by the following Equation 2.

$$\text{variance} = abs(R-RA) + abs(G-GA) + abs(B-BA) \quad \text{Equation 2}$$

In the Equation 2, 'R' is a saturation information for each pixel in the red image 1210, 'G' is a saturation information for each pixel in the green image 1220, and 'B' is a saturation information for each pixel in the blue image 1230. In addition, 'RA' is a saturation average for the first solder area in the red image 1210, 'GA' is a saturation average for the first solder area in the green image 1220, and 'BA' is a saturation average for the first solder area in the blue image 1230.

In the Equation 2, as difference between the saturation and the saturation average of the color image for each pixel become greater, the variance value of the associated pixel is detected greater, and as difference between the saturation and the saturation average of the color image for each pixel become smaller, the variance value of the associated pixel is detected smaller. That is, as the variance value for each pixel is smaller, possibility that the associated pixel corresponds to the solder is greater, and in contrast, as the variance value for each pixel is greater, possibility that the associated pixel corresponds to the solder is smaller.

Figure 11:
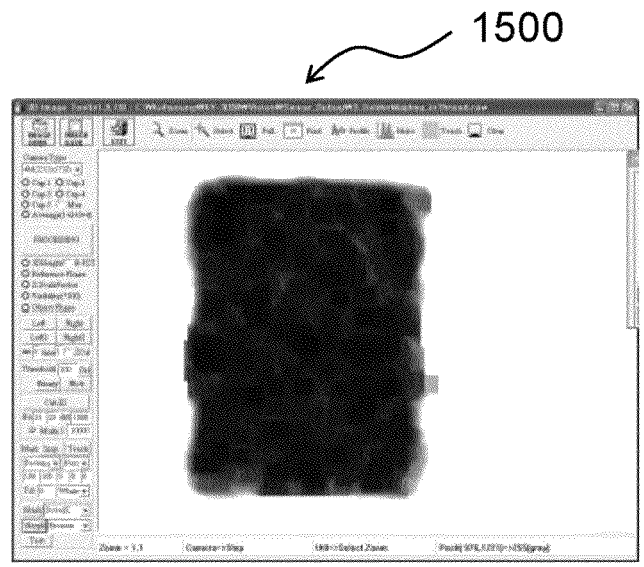
FIG. 11 is an image showing an example of a solder map.

Thereafter, the variance values for pixels in the variance map 1400 are compared to generate a solder map 1500 representing the second solder area in which the solder is substantially formed in step S1150. An example of the generated solder map 1500 is shown in FIG. 11.

A method of setting the second solder area may include setting an arbitrary critical value for the variance value by a user, judging that the associated pixel does not correspond to the solder area when the variance value for the associated pixel exceeds the critical value, and judging that the associated pixel corresponds to the solder area when the variance value for the associated pixel does not exceed the critical value. Meanwhile, in order to set the critical value for the variance value, an Otsu algorithm employing a statistical method may be used. The Otsu algorithm corresponds to a method including setting a cost function and regarding a value that gives the minimum value of the cost function as the critical value, in setting the critical value. When a gray value on an image is classified into two classes, since the distribution of the gray value on the image is displayed in a histogram, the critical value corresponds to a discrete level value in the histogram, and a portion below the level value may be classified into class 1 and a portion above the level value may be classified into class 2. Thus, class 1 may be judged as the solder area, and class 2 may be judged as an area that does not belong to the solder area, to thereby set the second solder area.

As described above, when the second solder area is set through the comparison in the variance map 1400, areas except for the solder area such as a pattern area may be effectively removed, so that the solder area may possibly be accurately set. In forming the solder map 1500, the solder map may be formed more accurately through a process of removing a small spot, a process of boundary weighting, etc.

Meanwhile, since the second illumination unit 1150 is disposed over the PCB in a circular form to illuminate the color illumination, the intensity may be non-uniformly detected for each area on the color image photographed in the image photographing section 1130. Color uniformity for each color illumination is corrected so as to reduce the non-uniformity of the intensity for each area, so that reliability for measuring the solder area may be enhanced.

Correcting the color uniformity for the color illuminations is performed before acquiring the color images in FIG. 8, and a compensation information for each color for correcting the color uniformity is generated through a gray target calibration, and intensity uniformity for each color may be corrected through the compensation information for each color.

Figure 12:
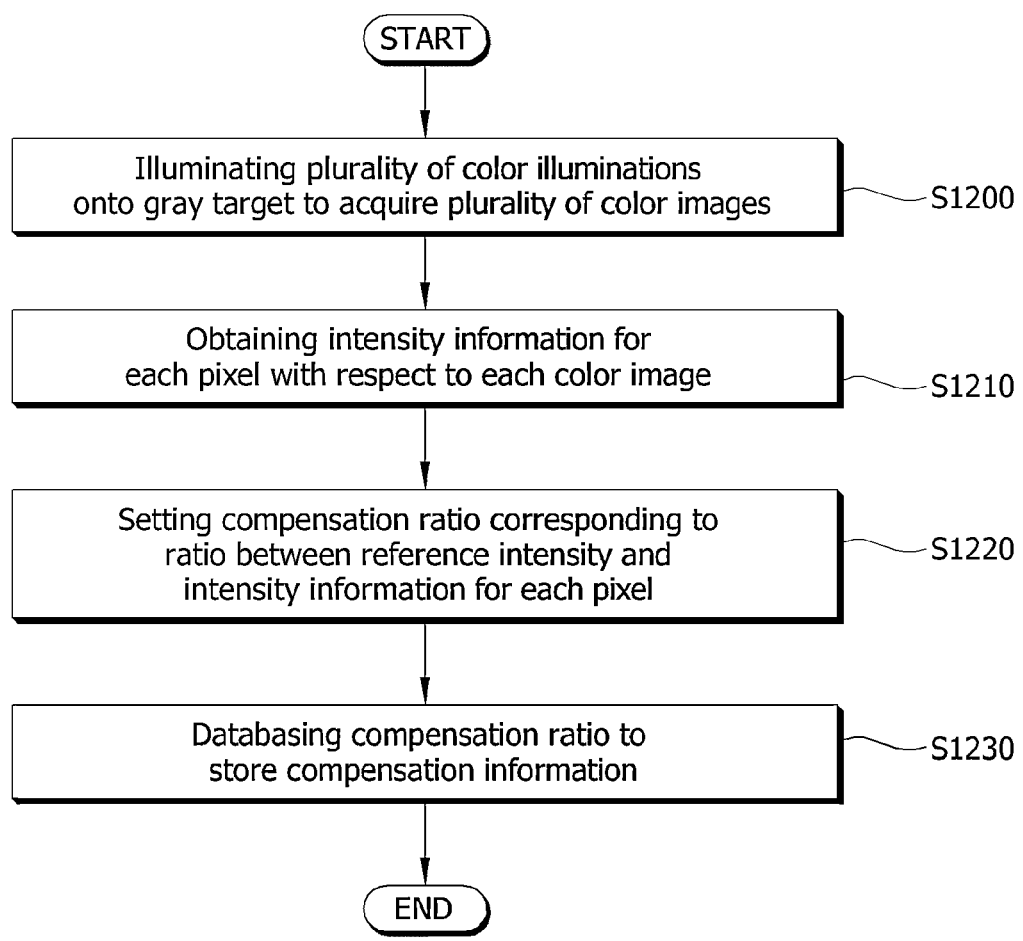
FIG. 12 is a flow chart showing a method of correcting color uniformity according to an exemplary embodiment of the present invention.
Figure 13:
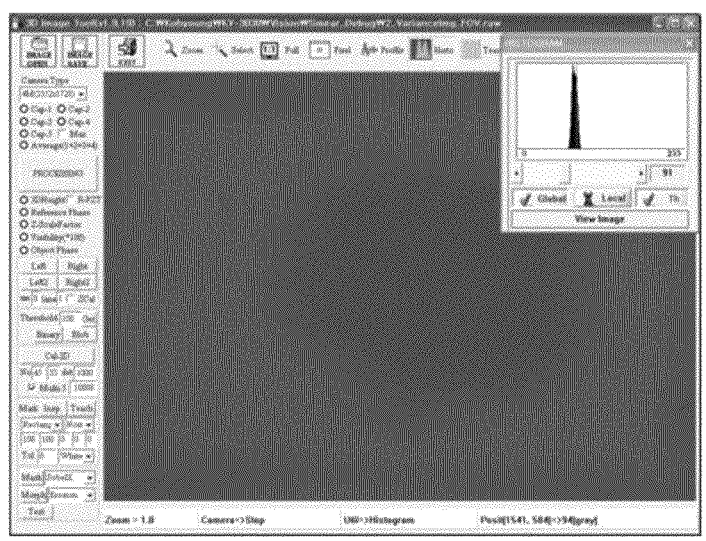
FIG. 13 is an image showing a red illumination acquired by employing a gray target as a target object.

FIG. 12 is a flow chart showing a method of correcting color uniformity according to an exemplary embodiment of the present invention. FIG. 13 is an image showing a red illumination acquired by employing a gray target as a target object.

Referring to FIGS. 6, 12 and 13, in order to correct the color uniformity, firstly, the color illuminations are illuminated onto a gray target to acquire a plurality of illumination images for each color in step S1200. That is, after the color illuminations are sequentially illuminated onto the gray target by using the second illumination unit 1150, the illumination images for colors corresponding to color illuminations is acquired by using the image photographing section 1130. For example, after the red illumination, the green illumination and the blue illumination are illuminated onto the gray target by using the red illumination part 1152, the green illumination part 1154 and the blue illumination part 1156 included in the second illumination unit 1150, a red illumination image, a green illumination image and blue illumination image are acquired corresponding to each color illumination.

For example, referring to FIG. 13 showing the acquired red illumination image, it may be confirmed that the intensity varies in locations within the field of view (FOV).

Then, the intensity for each pixel is obtained with respect to the illumination image for each color in step S1210. That is, the intensity information for each pixel is obtained from the red illumination image, the green illumination image and the blue illumination image, and stored.

Thereafter, a compensation ratio for each color, corresponding to a ratio between the intensity for each pixel and an arbitrary reference intensity, is set for each pixel in step S1220. The reference intensity may be set as an average intensity of the illumination image for each color. For example, an average intensity of total pixels within the field of view (FOV) of the illumination image for each color is set as the reference intensity. Alternatively, the reference intensity may be set as an arbitrary value that a user desires. For example, the compensation ratio for each color with respect to each pixel may be expressed as Equation 3.

compensation ratio=(average intensity of illumination image for each color)/(intensity of associated pixel)     Equation 3

Then, the compensation ratios for each color of total pixels within the field of view (FOV) are databased to generate and store the compensation information for each color in step S1230. The stored compensation information for each color may be used to increase accuracy of measuring the solder area, which is processed later. For example, after the color illuminations are illuminated onto the PCB to acquire the color images, before generating the saturation map by using the color images, each pixel of the color images is compensated for by using the compensation ratio for each color. That is, each pixel of the color images is multiplied by the compensation ratio for each color to compensate for the intensity non-uniformity of the color illumination itself, and reduce an error of measuring the solder area.

Meanwhile, according to characteristics of a solder ball included in the solder, deviation of intensity for each color may be generated within the solder area. In order to reduce the deviation of the intensity for each color of the solder, solder uniformity for the color illuminations may be corrected to enhance reliability of measuring the solder area.

Correcting the solder uniformity for the color illuminations may be performed before acquiring the color images shown in FIG. 8. Particularly, the color illuminations are illuminated onto the solder formed on the PCB to acquire solder images for each color. For example, after the red illumination, the green illumination and the blue illumination are illuminated onto the solder formed on the PCB by using the red illumination part 1152, the green illumination part 1154 and the blue illumination part 1156 included in the second illumination unit 1150, a red solder image, a green solder image and a blue solder image are acquired corresponding to each color illumination. Thereafter, the intensity for each color of the solder is obtained from each of the solder images for colors. That is, the intensity for each color of the solder is obtained from the red solder image, the green solder image and the blue solder image. The intensity for each color of the solder may be obtained from one pixel corresponding to the solder, or a plurality of pixels included in a predetermined area of the solder. Then, a compensation ratio for each color of the solder, corresponding to a ratio between the intensity for each color of the solder and an arbitrary reference intensity is set, and the set compensation ratio for each color of the solder is stored. The reference intensity may be set as an average intensity of a plurality of solder intensities for each color. For example, the reference intensity is set as an average intensity of a red solder intensity obtained from the red solder image, a green solder intensity obtained from the green solder image and a blue solder intensity obtained from the blue solder image.

The compensation ratio for each color of the solder acquired by the above described method may be used to increase accuracy of measuring the solder area, which is processed later. For example, after the color illuminations are illuminated onto the PCB to acquire the color images, before generating the saturation map by using the color images, the color images are compensated for by using the compensation ratio for each color of the solder. That is, each of the color images is multiplied by the compensation ratio for each color of the solder to compensate for the intensity non-uniformity for colors of the solder, and reduce an error of measuring the solder area.

Meanwhile, before acquiring the color images, the compensation ratio for each color of the color illuminations so as to correct the color uniformity for the color illuminations and the compensation ratio for each color of the solder so as to correct the solder uniformity for the color illuminations are set by the above described method in advance, and before generating the saturation map, each of the color images is multiplied by the compensation ratio for each color of the color illumination and the compensation ratio for each color of the solder, to thereby greatly enhance reliability of measuring the solder area.

As described above, the saturation map and the variance map are generated by using the color images obtained through the color illuminations, and the solder area is set by using the saturation map and the variance map, thereby increasing accuracy of measuring the solder area. In addition, before measuring the solder area, at least one process of correcting the color uniformity for the color illuminations and correcting the solder uniformity for the color illuminations is performed, thereby enhancing accuracy of measuring the solder area.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method of measuring a solder area on a printed circuit board (PCB) comprising:
    illuminating a plurality of color illuminations onto the PCB to acquire a plurality of color images;
    acquiring saturation information for each color through a color coordinate conversion of the color images;
    generating a saturation map by using the acquired saturation information for each color; and
    extracting a solder area by using the saturation map, wherein extracting the solder area by using the saturation map comprises:
        producing a saturation average for each color in the solder area;
        generating a variance map by using the saturation information for each color and the saturation average for each color; and
        comparing a variance value in the variance map with a critical value to generate a solder map representing the solder area in which a solder is formed.

2. The method of claim 1, wherein illuminating the color illuminations onto the PCB to acquire the color images comprising illuminating a red illumination, a green illumination and a blue illumination to acquire a red image, a green image and a blue image, respectively.

3. The method of claim 1, further comprising:
    acquiring intensity information for each color through the color coordinate conversion of the color images.

4. The method of claim 3, wherein extracting the solder area by using the saturation map comprising excluding at least one of a wiring pattern area and a dark solder resist area from the saturation map by using the intensity information for each color and setting the solder area.

5. The method of claim 1, wherein each of the variance values for pixels is acquired by the following equation:

$$\text{variance value for each pixel} = abs(R-RA) + abs(G-GA) + abs(B-BA),$$

wherein 'R', 'G' and 'B' are saturation informations for each pixel, and 'RA', 'GA' and 'BA' are saturation averages for each color.

6. The method of claim 1, prior to illuminating the color illuminations onto the PCB to acquire the color images, further comprising:
    illuminating the color illuminations onto a target to acquire a plurality of illumination images for colors;
    obtaining an intensity for each pixel with respect to each of the illumination images for colors; and
    setting a compensation ratio for each color, corresponding to a ratio between the intensity for each pixel and an arbitrary reference intensity, for each pixel, and
    prior to acquiring saturation information for each color through a color coordinate conversion of the color images, further comprising compensating for the color images by using the compensation ratio for each color.

7. The method of claim 6, wherein the reference intensity corresponds to an average intensity of each of the color images.

8. The method of claim 1, prior to illuminating the color illuminations onto the PCB to acquire the color images, further comprising:
    illuminating the color illuminations onto a solder formed on the PCB to acquire a plurality of solder images for each color;
    obtaining an intensity for each color of the solder from each of the solder images for each color; and
    setting a compensation ratio for each color of the solder, corresponding to a ratio between the intensity for each color of the solder and an arbitrary reference intensity, and
    prior to acquiring saturation information for each color through a color coordinate conversion of the color images, further comprising compensating for the color images by using the compensation ratio for each color of the solder.

9. The method of claim 8, wherein the reference intensity corresponds to an average intensity of a plurality of solder intensities for each color.

10. The method of claim 1, prior to illuminating the color illuminations onto the PCB to acquire the color images, further comprising:

setting a compensation ratio for each color of the color illuminations to correct color uniformity for the color illuminations; and setting a compensation ratio for each color of a solder to correct solder uniformity for the color illuminations, and prior to acquiring saturation information for each color through a color coordinate conversion of the color images, further comprising multiplying each color image by the compensation ratio for each color of the color illuminations and the compensation ratio for each color of the solder.

* * * * *